(12) United States Patent  
Fuchs

(10) Patent No.: US 12,629,389 B2  
(45) Date of Patent: *May 19, 2026

(54) PHARMACEUTICAL PREPARATION CONTAINING SELENITE OR SELENITE-CONTAINING COMPOUNDS FOR TREATING CERVICAL DYSPLASIA OR CARCINOMAS

(71) Applicant: SELO MEDICAL GMBH, Unternberg (AT)

(72) Inventor: Norbert Fuchs, Mariapfarr (AT)

(73) Assignee: SELO MEDICAL GMBH, Unternberg (AT)

( * ) Notice: Subject to any disclaimer, the term of this patent is extended or adjusted under 35 U.S.C. 154(b) by 768 days.

This patent is subject to a terminal disclaimer.

(21) Appl. No.: 16/738,797

(22) Filed: Jan. 9, 2020

(65) Prior Publication Data

US 2020/0206262 A1 Jul. 2, 2020

Related U.S. Application Data

(63) Continuation of application No. 16/225,263, filed on Dec. 19, 2018, now Pat. No. 10,543,228, which is a continuation of application No. 14/000,133, filed as application No. PCT/AT2012/000032 on Feb. 16, 2012, now Pat. No. 10,201,566.

(30) Foreign Application Priority Data

Feb. 16, 2011 (AT) .................................. A 201/2011

(51) Int. Cl.

| | |
|---|---|
| *A61K 33/04* | (2006.01) |
| *A61K 9/00* | (2006.01) |
| *A61K 9/06* | (2006.01) |
| *A61K 45/06* | (2006.01) |
| *A61K 47/38* | (2006.01) |

(52) U.S. Cl.  
CPC ............ *A61K 33/04* (2013.01); *A61K 9/0034* (2013.01); *A61K 9/0036* (2013.01); *A61K 9/06* (2013.01); *A61K 45/06* (2013.01); *A61K 47/38* (2013.01)

(58) Field of Classification Search  
CPC ..... A61K 33/04; A61K 9/0034; A61K 9/0036  
See application file for complete search history.

(56) References Cited

U.S. PATENT DOCUMENTS

| | | |
|---|---|---|
| 4,512,977 A | 4/1985 | Lundy |
| 4,668,515 A | 5/1987 | Bankit et al. |
| 4,681,753 A | 7/1987 | Revici |
| 4,762,726 A | 8/1988 | Soucie et al. |
| 5,153,230 A | 10/1992 | Jaffery |
| 5,182,104 A | 1/1993 | Marcus et al. |
| 5,425,944 A | 6/1995 | Harich |
| 5,470,880 A | 11/1995 | Yu et al. |
| 5,512,200 A | 4/1996 | Garcia |
| 5,536,497 A | 7/1996 | Evans et al. |
| 5,999,844 A * | 12/1999 | Gombrich .............. A61B 5/065 |
| | | 600/109 |
| 6,069,152 A | 5/2000 | Schaus et al. |
| 6,114,348 A | 9/2000 | Weber et al. |
| 6,120,758 A | 9/2000 | Siddiqui et al. |
| 6,133,237 A | 10/2000 | Noll et al. |
| 6,277,835 B1 | 8/2001 | Brown |
| 6,391,323 B1 | 5/2002 | Carnevali |
| 2003/0180387 A1 | 9/2003 | Kossler et al. |
| 2004/0265355 A1* | 12/2004 | Shalaby .................. A61L 31/16 |
| | | 424/426 |
| 2005/0048134 A1* | 3/2005 | Kuklinski .............. A61P 17/16 |
| | | 514/561 |
| 2013/0323328 A1 | 12/2013 | Fuchs |

FOREIGN PATENT DOCUMENTS

| | | |
|---|---|---|
| CA | 2468906 | 6/2003 |
| CN | 1529606 | 9/2004 |
| CN | 103379899 | 10/2013 |
| DE | 3408362 | 9/1984 |
| DE | 4320694 | 1/1995 |
| DE | 4335441 | 4/1995 |
| DE | 4413839 | 10/1995 |
| EG | 2007/030129 | 3/2007 |
| EP | 0000670 | 2/1979 |
| EP | 0750911 | 1/1997 |
| EP | 0913155 | 5/1999 |
| FR | 2779720 | 12/1999 |
| GB | 2323030 | 9/1998 |
| JP | 2004518758 | 6/2004 |
| JP | 2014505708 | 3/2014 |

(Continued)

OTHER PUBLICATIONS

Syed et al.*  
Crowley, M.M. "Solutions, Emulsions, Suspensions, and Extracts" Chapter 39. Remington: The Science and Practice of Pharmacy, 21st Edition, 2005, 745-775. (Year: 2005).*  
Hong et al. "Detection of level of slenium in cervical tissues of patients with human papillomavirus infection" Zhongguo Redai Yixue (2008), 8(8), 1315-1316 (English abstract) (Year: 2008).*

(Continued)

*Primary Examiner* — Andrew S Rosenthal

(74) *Attorney, Agent, or Firm* — Norton Rose Fulbright US LLP

(57) ABSTRACT

The invention relates to compositions containing selenite-containing compounds and pharmaceutically acceptable acids, selected from citric acid, acetic acid, malic acid, carbonic acid, sulphuric acid, nitric acid, hydrochloric acid, fruit acids or mixtures thereof, for use for treating cervical inflammations, dysplasia and/or carcinomas. The invention further relates to methods of using such compositions.

18 Claims, No Drawings

(56) References Cited

FOREIGN PATENT DOCUMENTS

| TW | 201309308 | 3/2013 |
|----|-----------|--------|
| WO | WO 2000/012101 | 3/2000 |
| WO | WO 2000/028977 | 5/2000 |
| WO | WO 2001/085852 | 11/2001 |
| WO | WO 2001/093910 | 12/2001 |
| WO | WO 2002/072112 | 9/2002 |
| WO | WO 2003/047604 | 6/2003 |
| WO | WO 2005/048925 | 6/2005 |
| WO | WO 2012/109685 | 8/2012 |

OTHER PUBLICATIONS

Kim, S.Y. et al. "Changes in Lipid Peroxidation and Antioxidant Trace Elements in Serum of Women With Cervical Intraepithelial Neoplasia and Invasive Cancer" Nutrition and Cancer vol. 47, Issue 2, 2003, pp. 126-130 (Year: 2003).*

Medline (http://www.nlm.nih.gov/medlineplus/ency/article/001491. htm as published Dec. 31, 2009) (Year: 2009).*

"Bromelains," Reynolds JEF (Editor). Martindale: The Extra Pharmacopeia (Twenty-Eight Edition). The Pharmaceutical Press, London, pp. 646, 1982.

"Hydroxy Acid," Stedman's Medical Dictionary (Twenty-Second Edition). Williams and Wilkins Company, pp. 595, 1972.

"Melanoma," The Merck Manual-Second Home Edition [Online] 1995-2000.

"Preventive" and "Prophylactic," Stedman's Medical Dictionary (Twenty-Second Edition). Williams and Wilkins Company, pp. 1017, 1025, 1972.

"Supplementation" (http://www.thefreedictionary.com/supplementation) Accessed Jan. 31, 2017, p. 1.

"Vitamin C," Stedman's Medical Dictionary (Twenty Fifth Edition). Williams and Wilkins, pp. 1725-1726, 1990.

Carey, "Carbonic Acid," Organic Chemistry (Fourth Edition). McGraw Hill, pp. 749, 2000.

Crowley, M.M. "Solutions, Emulsions, Suspensions, and Extracts" Chapter 39. Remington: The Science and Practice of Pharmacy, 21st Edition, 2005, 745-775.

Eisenberg et al., ""Interactions of Selenium and Fluoride on Growth, Glycolysis and Survival of Streptococcus mutans GS-5"", Caries Research, 1990, 24, 306-311.

Emmert, "Treatment of Common Cutaneous Herpes Simplex Virus Infections," American Family Physician, 61:1697-1706, 1708, 2000.

English et al., "Dermatoses of the glans penis and prepuce" Journal of the American Academy of Dermatology, 37(1): 1-24, 1997 (Abstract).

Fu et al., "Proteomic study on sodium selenite-induce apoptosis of human cervical cancer HeLa cells" Journal of Trace Elements in Medicine and Biology, 2011, 25(3): 130-137.

Ganther, "Metabolism of hydrogen selenide and methylated selenides," Advances in Nutrional Research, Draper HH, editor, New York—Plenum Press, 2:107-128, 1979.

Gonzalez, "Ascorbic Acid and Selenium Interaction: Its Relevance in Carcinogenesis", Journal of Orthomolecular Medicine, vol. 5, No. 2, 1990, pp. 67-69.

Haas et al., "The Pathogenesis of Hemorrhoids" Dis Colon Rectum, 27: 442-50. 1984.

Hong et al., "Detection of level of selenium in cervical tissues of patients with human papillomavirus infection" Zhongguo Redai Yixue, 2008, 8(8):1315-1316. (English Abstract).

Hussain et al., "Chemopreventive Action of Selenium on Methylcholanthrene-Induced Carcinogenesis in the Uterine Cervix of Mouse" Oncology, 49: 237-240, 1992.

International Preliminary Report on Patentability issued in PCT Application No. PCT/AT2012/00032, dated Aug. 21, 2013.

International Search Report issued in PCT Application No. PCT/AT2012/00032, mailed Apr. 4, 2012.

Introduction to modern pharmaceuticals (3rd edition), Apr. 10, 1987, p. 414-416 (published in Japanese).

Ismail et al., "Prevention of periodontal disease," Canadian Task Force on the Periodic Health Examination, Canadian Guide to Clinical Preventive Health Care, Ottawa: Health Canada, 420-431, 1994.

Ju et al., "Sodium Selenite Induced HeLa Cells Apoptosis" J. Wuhan Univ. (Nat. Sci. Ed.) 2005, 51(6), 663-667.

Kim et al., "Changes in Lipid Peroxidation and Antioxidant Trace Elements in Serum of Women with Cervical Intraepithelial Neoplasia and Invasive Cancer" Nutrition and Cancer, 2003, 47(2):126-130.

Liang et al., "Sodium Selenite Induced HeLa Cells Apoptosis", Nat Sci Ed., 2005, 51(6):663-667. (Chinese)—[English Abstract provided].

Lutsoia et al., "Correlation of the Nitrate and Ascorbic Acid Content in Vegetables and Fruit," Vopr. Pitan., 3:54-57, 1980 (Abstract).

Manola et al., "Prognostic Factors in Metastatic Melanoma: A Pooled Analysis of Eastern Cooperative Oncology Group Trials," Journal of Clinical Oncology, 18:3782-3793, 2000.

Margolis, "Therapy for Condyloma Acuminatum: A Review", Reviews of Infections Diseases, 4 supplement, S829-S836, 1982.

Maron, "Enamel erosion resulting from hydrochloric acid tablets," JADA, 127:781-784, 1996.

MayoClinic.com, "Periodontitis," Mayo Foundation for Medical Education and Research (MFMER), http://www.mayoclinic.com/health/periodontitis/DS00369/DSECTION=3, 2006.

Mcbride et al., "Role of Interbacterial Adherence in Colonization of the Oral Cavities of the Gnotobiotic Rats Infected with Streptococcus mutans and Veillonella alcalescens," Immunity and Infection, 33(2): 467-472, 1981.

Medline http://www.nlm.nih.gov/medlineplus/ency/article/001491. htm as published Dec. 31, 2009.

Merck Manual Home Edition: Periodontitis.

National Cancer Institute: definition of Fruit Acid, obtained from the internet at http://www.cancer.gov/dictionary/?CdriD=613195 on Aug. 2, 2010.

Novotny et al., "Impact of ascorbic acid on selenium-induced growth inhibition of canine mammary tumor cells in vitro," J. Nutr. Biochem., 4:341-345, 1993.

Office Action issued in corresponding Chinese application No. 201710854416.3, dated Feb. 17, 2020.

Office Communication issued in Austrian Patent Application No. A 201/2011, dated Sep. 6, 2011.

Office Communication issued in U.S. Appl. No. 10/497,504 dated Oct. 27, 2006.

Office Communication issued in U.S. Appl. No. 10/497,504 dated Jan. 3, 2007.

Office Communication issued in U.S. Appl. No. 10/497,504 dated Aug. 17, 2007.

Office Communication issued in U.S. Appl. No. 10/497,504 dated Jul. 16, 2008.

Office Communication issued in U.S. Appl. No. 10/497,504, dated Dec. 8, 2008.

Office Communication issued in U.S. Appl. No. 10/497,504, dated Jul. 31, 2009.

Perry, "Handbook of Inorganic Compounds," Taylor & Francis Group, Second Edition, 2011, pp. 548.

Rotruck, "Discovery of the Role of Selenium in Glutathione Peroxide," Selenium in Biology and Medicine, Eds. Spallholz, Martin, Ganther, AVI Publishing Co., pp. 10-16, 1981.

Rudolf et al., "Selenium activates p53 and p38 pathways and induces caspase-independent cell death in cervical cancer cells", Cell Biology and Toxicology, 2007, 24(2):123-141.

Schiffman et al, "Human papillomavirus and cervical cancer" The Lancet, 2007, 370:890-907.

Socransky, "Relationship of Bacteria to the Etiology of Peridontal Disease," Journal of Dental Research, 49(2): 203-222, 1970.

Lipinski, "Rationale For the Treatment of Cancer with Sodium Selenite," Medical Hypothesis, 64(4): 806-810, 2005, (English Abstract).

Office Action Issued in Corresponding Egyptian Patent Application No. 2013081314, dated Jan. 28, 2020.

Hong et al., "Detection of level of selenium in cervical tissues of patients with human papillomavirus infection" China Tropical Medicine 2008, 8(8), 6 pages (Full English Translation provided).

(56)                References Cited

OTHER PUBLICATIONS

Zhengping et al. "10-year follow-up of the dynamic changes of HBV serum markers in chronic hepatitis B patients after selenium supplementation" Trace Elements and Health Research, Issue 6, 2007, https://www.cqvip.com/gk/91209x/200706/25934991.html. Accessed Jul. 22, 2022 (Machine Translation of Abstract provided).

Kim, J.H. et al., A pilot study to investigate the treatment of cervical human papillomavirus infection with zinc-citrate compound (CIZAR®), *Gynecologic Oncology*, 122(2): pp. 303-306, 2011.

Office Action issued in corresponding Japanese Application No. 2021-510859, dated Jun. 27, 2023. (English Translation Provided).

Benevolo et al. "Immunohistochemical expression of p16INK4a is predictive of HR-HPV infection in cervical low-grade lesions", Modern pathology 19, pp. 384-391 2006.

De Villers et al., "Classification of papillomaviruses", *Virology*, 324:17-27, 2004.

Extended European Search Report issued in corresponding Application No. 18191289.0 dated Mar. 6, 2019.

International Search Report and Written Opinion issued in corresponding PCT/EP2019/072926 mailed on Oct. 29, 2019.

Jing et al., "HPV genotypes and associated cervical cytological abnormalities in women from the Pear River Delta region of Guagdong province, China: a cross-sectional study", *BMC Infectious Diseases* 2014, 14:388, 9 pages.

Keating JT. et al. Cyclin E, and p16INK4a are complimentary surrogate biomarkers for human papilloma virus-related cervical neoplasia. Am J Surg Pathol; 25: pp. 84-891, 2001.

Ravarino et al., "CINtec Plus Immunocytochemistry as a Tool for the Cytologic Diagnosis of Glandular Lesions of the Cervix Uteri", *Am J Clin pathol.*, 138(5): 652-656, 2012.

Lim et al., "Efficacy of p16 and Ki 67 immunostaining in the detection of squamous intraepithelial lesions in a high risk HPV group", *Oncology Letters*, vol. 11, pp. 1447-1452, 2016.

Office Action issued in corresponding Taiwanese Application No. 11220586940, dated Jun. 20, 2023. (English Translation).

Office Action issued in corresponding Chinese Application No. 201980055480., dated Apr. 15, 2023. (English Translation).

Graham et al., "Clinical Investigation: Phase II Trial of β-All-trans-Retinoic Acid for Cervical Intraepithelial Neoplasia Delivered via a Collagen Sponge and Cervical Cap", *The Western Journal of Medicine*, Aug. 1986, pp. 192-195.

Helm et al., "Retinoids for preventing the progression of cervical intra-epithelial neoplasia", *Cochrane Database of Systematic Reviews*, 2013, 21 pages.

Meyskens, Jr. et al, "A Phase I Trial of B-all-trans-Retinoic Acid Delivered via a Collagen Sponge and a Cervical Cap for Mild or Moderate Intraepithelial Cervical Neoplasia", *JNCI*, vol. 71, No. 5, Nov. 1983, pp. 921-925.

Peng, et al.,"Cervical tissue uptake of all-trans-retinoic acid delivered via a collagen sponge-cervical cap delivery device in patients with cervical dysplasia", *Investigational New Drugs*, 4, 1986, pp. 245-249.

\* cited by examiner

PHARMACEUTICAL PREPARATION CONTAINING SELENITE OR SELENITE-CONTAINING COMPOUNDS FOR TREATING CERVICAL DYSPLASIA OR CARCINOMAS

CROSS-REFERENCE TO RELATED APPLICATIONS

This application is a continuation of U.S. application Ser. No. 16/225,263 filed 19 Dec. 2018, which issued as U.S. Pat. No. 10,543,228 on 28 Jan. 2020, which is a continuation of U.S. application Ser. No. 14/000,133 filed 16 Aug. 2013, which issued as U.S. Pat. No. 10,201,566 on 12 Feb. 2019, which is a national phase application under 35 U.S.C. § 371 of International Application No. PCT/AT2012/000032 filed 16 Feb. 2012, which claims priority to Austrian Application No. A 201/2011 filed 16 Feb. 2011. The entire contents of each of the above-referenced disclosures is specifically incorporated herein by reference without disclaimer.

BACKGROUND OF THE INVENTION

The present invention relates to pharmaceutical compositions containing selenite-containing compounds.

Inflammatory and/or degenerative alterations of the female cervix are a steadily increasing public health problem. Testing of cervical cell smears was developed by the Greek physician George Papanicolaou and the smears are classified according to the so-called Munich nomenclature II. Herein, the classification PAP I corresponds to a normal result, PAP II to a minor inflammatory and/or degenerative alteration, PAP III to cell profiles that cannot be assessed and need to be monitored, PAP IIID to a dysplasia, PAP IV to serious preliminary stages of carcinoma, and PAP V to a malign tumor. The forms of dysplasia PAP IIID and PAP IV are cytologically further differentiated into so-called "cervical intraepithelial neoplasias" (CIN) with the stages of CIN 1 for minor, CIN 2 for moderate, and CIN 3 for severe dysplasia. Analogously to the histological classification from CIN 1 (PAP IIID) to CIN 2 (also PAP IIID) to CIN 3 (PAP IV), it is also referred to the so-called Bethesda classification in the Anglo-American part of the world. Herein, the "Low-Grade Squamous Intraepithelial Lesion" (LSIL) corresponds to the Munich classification CIN 1, whereas cell alterations of a higher grade, i.e., "High-Grade Squamous Intraepithelial Lesions" (HSIL), correspond to the WHO classifications CIN 2 and CIN 3.

The average tendency for the regression of minor dysplasias (PAP IIID/CIN 1/LSIL) to a normal result (PAP I and PAP II, respectively) within a one-year period is as low as almost 15%. The tendency for the progression of minor dysplasias (PAP IIID/CIN 1/LSIL) to higher-grade dysplasias currently exhibits a mean annual transition probability of more than 7%, while the progression tendency of higher-grade dysplasias to carcinomas of the uterus is 0.74%.

Depending on the location and the severity of the cell alterations, the current international gynecological guidelines for the therapy of Cervical Intraepithelial Neoplasias (CIN) and microcarcinomas of the *Cervix uteri* comprise a destruction of the surface of the affected tissue, a conization with the aid of a scalpel, laser or LEEP (Loop Electrosurgical Excision Procedure) or a hysterectomy. Other non-surgical therapies are not known to date.

On the electrochemical level, inflammatory tissue processes are always associated with a (local) increase in so-called Reactive Oxygen Species (ROS), i.e., free radicals and peroxides. In the context of a spontaneous amelioration of these oxidative inflammatory factors, the competence of the body's own immune system and the levels of endogenous and exogenous antioxidants in the body play an important biological role. The anti-inflammatory and anti-viral effects of antioxidative compositions have already been verified in numerous scientific publications and international patent documents (i. a. WO 2001/093910 A2 and WO 2003/047604 A1).

SUMMARY OF THE INVENTION

It was the object of the present invention to provide new means for the prevention and treatment of inflammations, dysplasias and/or carcinomas of the cervix.

Accordingly, the present invention relates to a pharmaceutical composition containing selenite-containing compounds and pharmaceutically acceptable acids, selected from citric acid, acetic acid, malic acid, carbonic acid, sulfuric acid, nitric acid, hydrochloric acid, fruit acids (e.g., malic acid, citric acid, tartaric acid, oxalic acid and fumaric acid, in particular citric acid) or mixtures thereof, for use in the treatment of inflammations, dysplasias and/or carcinomas of the cervix.

In the context of the present invention, it could surprisingly be found that a consequent local administration of antioxidative selenium-containing preparations (according to WO 2001/093910 A2 and WO 2003/047604 A1) in vivo also has a positive influence on negative cell alterations (dysplasias and carcinomas) within the scope of an early detection of cervical carcinoma. The present invention is suitable for both HPV-induced and non-HPV-induced disorders of the uterus. This is of great practical significance as the detection, or even specification, of the HPV is often omitted in gynecological practice because the positive detection of an HPV infection often has no influence on subsequent therapeutic decisions. However, the inventive treatment of non-HPV-induced uterine disorders (i.e., the use of the preparations according to the present invention in the treatment of or as a medication for inflammations, dysplasias and/or carcinomas of the cervix) is a particularly preferred embodiment of the present invention. Consequently, the present invention does not represent a strategy that is directed against a specific pathogen, but rather aims at a treatment of inflammations, dysplasias and/or carcinomas of the cervix in a directed manner, i.e., it may also be employed (long) after a potential pathogen has elicited the symptoms of a disease.

It has shown that a composition having an enhanced antioxidative potential may be provided by adding the above-mentioned acids to aqueous solutions of inorganic selenium compounds. Herein, the compositions prepared according to the present invention, i.e., in particular solutions, gels, emulsions, suspensions, ointments and the like, exhibit the therapeutic effects according to the present invention as—owing to the presence of the acids—they may be used in accordance with the present invention such as to, at least temporarily, maintain said enhanced antioxidative potential. This is the case if the enhanced antioxidative potential is still present at the time of administration at the therapy target destination and has not already been diluted, e.g., by administration solutions or body fluids, such as blood (e.g., in case of intravenous administration) or contents of the digestive tract (e.g., in case of oral application).

Accordingly, the present invention preferably relates to the topical, mucosal and intravaginal administration of these preparations for external use (i.e., topical or buccal) or for the direct administration to mucous membranes (mucosal application). Typical formulations for administration that are suitable for a topical, mucosal or intravaginal administration are known to a person skilled in the art and have been described in the relevant pharmacopoeias.

In addition to the essential ingredients of selenite and the above-mentioned acids, the composition according to the present invention may also contain further suitable ingredients and/or pharmaceutically acceptable excipients. The composition according to the present invention preferably contains selenite in an amount between 1 and 500 mg, more preferably between 10 and 100 mg, in particular between 30 and 70 mg, per 100 g of the composition. Preferably, the composition according to the present invention contains selenite in the form of sodium selenite (which is mostly present as a pentahydrate compound which starts to release crystal water at 40° C.).

Independently, the composition according to the present invention preferably contains one or more acids in a total amount between 1 mg and 10 g acid, more preferably between 10 mg and 5 g acid, in particular between 100 mg and 1 g acid, per 100 g of the composition (in particular if the acid is added in its solid form). Alternatively, the acid may also be added in its liquid form (e.g., with water, i.e., as an aqueous solution). Water and aqueous solutions, respectively, optionally containing further ingredients, may be added to the composition according to the present invention in an amount between 0 and (about) 99.9 g, preferably between 50 and 99 g, in particular between 80 and 98 g, per 100 g of the composition.

According to a preferred embodiment, the present invention is provided in the form of a gel. Accordingly, the composition according to the present invention preferably contains a gelling agent. Both inorganic and organic aqueous gelling agents may be used as a gelling agent. Particularly suitable gelling agents are cellulose derivatives, in particular carboxymethylcellulose, methylcellulose, hydroxypropyl-cellulose and, in particular, hydroxyethylcellulose. Preferably, the gelling agents, in particular hydroxyethylcellulose, are used at a total concentration of between 0.1 g and 30 g, more preferably between 0.5 g and 5 g, in particular between 1 g and 3 g, per 100 g of the composition.

A particularly preferred embodiment of the gel composition according to the present invention contains silicon dioxide, in particular highly dispersed silicon dioxide, e.g., according to WO 2001/85852 A1, as a technological suspension medium and/or as an adsorbent. Preferably, an amount between 100 mg and 50 g, more preferably between 500 mg and 10 g, in particular between 1 g and 5 g, $SiO_2$ per 100 g of the composition is used.

The composition according to the present invention preferably has a pH-value of less than 7.0, more preferably less than 5.0, in particular between 4.0 and 2.5.

The composition according to the present invention is preferably present in the form of a solution, emulsion, ointment or sponge (tampon). Advantageously, the composition may contain further excipients and/or further active ingredients, in particular buffer substances, coloring agents, stabilizers, preservatives, carrier substances or combinations thereof. Preferred examples of such substances are malto-dextrin, flavoring agents, such as e.g., lemon flavor, pepper-mint oil, potassium sorbate and sodium benzoate (as preservatives), and the like.

Preferred further active ingredients are antibiotics, anti-viral agents, antimycotics, pain inhibitors, anti-inflammatory agents or combinations thereof.

The composition according to the present invention has surprisingly proved to be particularly effective in the treatment of cervical cell alterations having a PAP score of ≥PAP III and/or a CIN score of ≥CIN 1. In particular, the present invention may be used in the treatment of cervical inflammations having a PAP score of PAP III and PAP IIID.

Furthermore, it is to be pointed out that the present invention is suitable for the treatment of cervical carcinomas.

According to a further aspect, the present invention relates to a method for the treatment of inflammations, dysplasias and/or carcinomas of the cervix, in which the compositions according to the present invention are administered in an effective amount to patients suffering from the above disorders. Preferred dosages may range (e.g., when present as a gel) between 0.005 g and 0.1 g of sodium selenite penta-hydrate per 100 g of the gel, in particular between 0.01 g and 0.1 g per 100 g of the gel.

DETAILED DESCRIPTION

The present invention will be explained in more detail by way of the following Examples, without being limited thereto.

Example 1: Preparation of an Acidified Sodium Selenite Gel

An acidified sodium selenite gel was prepared in the following composition (per 100 g):

| | |
|---|---|
| Sodium selenite pentahydrate | 0.050 g |
| Silicon dioxide, highly dispersed | 0.200 g |
| Citric acid | 0.496 g |
| Sodium benzoate | 0.050 g |
| Potassium sorbate | 0.099 g |
| Hydroxyethylcellulose | 1.985 g |
| Water | 97.120 g |
| | 100.000 g |

Example 2: Treatment of Cervical Dysplasias

Design: Multicenter pilot study

Inclusion criteria: Age>19 years

PAP≥III<IV

Implementation

Intravaginal administration of 5 ml of sodium selenite gel 1× per day in case of a diagnosis of PAP≥III<IV over a period of 90 days. The administration is to be discontinued during menstruation. Follow-up examination after 90 days of gel administration.

Results

Of 31 patients 27 (87.1%) exhibited a response; 4 patients (12.9%) were non-responders.

Example 3: Effects of the Acidified Sodium
Selenite Gel

| Initials | Age | First ward round | Last ward round | PAP start | PAP end | HPV start | HPV end |
|---|---|---|---|---|---|---|---|
| CC | 45 | Jul. 15, 2010 | Oct. 5, 2010 | III D | II | neg. | n.d. |
| AU | 47 | Jul. 20, 2010 | Oct. 12, 2010 | III D | II | n.d. | n.d |
| IG | 28 | Jul. 20, 2010 | Sep. 9, 2010 | IV | IV | pos. | n.d. |
| NK | 34 | Aug. 3, 2010 | Nov. 3, 2010 | III D | III | neg. | n.d. |
| KS | 44 | Aug. 3, 2010 | Nov. 3, 2010 | III | III | neg. | n.d. |
| RS | 19 | Jul. 21, 2010 | Oct. 28, 2010 | III D | III D | pos. | pos. |
| BK | 49 | Jul. 27, 2010 | Oct. 27, 2010 | III D | II | pos. | n.d. |
| MJ | 42 | Jul. 27, 2010 | Oct. 27, 2010 | III D | II | n.d. | n.d. |
| AU | 19 | Apr. 14, 2010 | Nov. 3, 2010 | III D | II | pos. | n.d. |
| TF | 25 | Jul. 28, 2010 | Oct. 28, 2010 | III D | II | pos. | neg. |
| RH | 49 | Jul. 28, 2010 | Oct. 28, 2010 | III D | II | n.d. | n.d. |
| SH | 32 | Jul. 29, 2010 | Nov. 2, 2010 | III D | II | pos. | n.d. |
| AK | 27 | Aug. 2, 2010 | Nov. 3, 2010 | III D | II | pos. | n.d. |
| SL | 27 | Jul. 29, 2010 | Oct. 29, 2010 | III | II | pos. | n.d. |
| AG | 71 | Aug. 2, 2010 | Nov. 4, 2010 | III | II | n.d. | pos. |
| ER | 28 | Aug. 26, 2010 | Nov. 2, 2010 | III D | II | pos. | pos. |
| BS | 53 | May 10, 2010 | Sep. 30, 2010 | III D | III D | pos. | n.d. |
| RS | 52 | Jun. 23, 2010 | Nov. 11, 2010 | III | III | neg. | neg. |
| DG | 48 | May 18, 2010 | Nov. 2, 2010 | III D | II | n.d. | n.d. |
| MJ | 19 | May 10, 2010 | Aug. 9, 2010 | III D | II | pos. | neg. |
| RM | 62 | May 27, 2010 | Oct. 6, 2010 | III | II | n.d. | n.d. |
| AF | 38 | Jun. 22, 2010 | Aug. 16, 2010 | III D | II | pos. | n.a. |
| MF | 49 | Jul. 28, 2010 | Jun. 30, 2010 | III D | II | pos. | pos. |
| PK | 56 | May 26, 2010 | Nov. 2, 2010 | III D | II | neg. | n.d. |
| IR | 41 | Jun. 8, 2010 | Aug. 17, 2010 | III | IV | n.d. | n.d. |
| BP | 56 | Jun. 14, 2010 | Nov. 3, 2010 | III D | II | pos. | n.a. |
| EN | 47 | Jun. 2, 2010 | Nov. 11, 2010 | III D | II | pos. | n.a. |
| IP | 40 | Jul. 26, 2010 | Aug. 26, 2010 | III D | II | pos. | n.a. |
| MW | 47 | Jul. 26, 2010 | Aug. 26, 2010 | III D | n.d. | n.d. | n.a. |
| MR | 50 | Aug. 2, 2010 | Sep. 2, 2010 | III D | IV | pos. | n.a. |
| DB | 22 | Jul. 8, 2010 | Nov. 11, 2010 | III | II | pos. | n.a. |
| YT | 32 | Aug. 19, 2010 | Nov. 11, 2010 | III | II | n.d. | n.a. |
| KP | 67 | Aug. 10, 2010 | Nov. 13, 2010 | III | II | neg. | n.d. |
| RK | 45 | Jun. 24, 2010 | Sep. 20, 2010 | III | II | neg. | neg. |
| CS | 50 | Aug. 30, 2010 | Nov. 8, 2010 | III | III | n.d. | n.a. |
| ML | 28 | Aug. 3, 2010 | Nov. 3, 2010 | III | II | neg. | |
| FP | 43 | Aug. 10, 2010 | Nov. 11, 2010 | III D | II | pos. | n.d. |
| CD | 44 | Sep. 7, 2010 | Dec. 14, 2010 | III D | II | pos. | n.d. |
| KW | 21 | Aug. 12, 2010 | Nov. 30, 2010 | III D | III D | pos. | n.d. |
| EL | 52 | Aug. 13, 2010 | Nov. 18, 2010 | III | II | n.d. | n.d. |
| ES | 38 | Aug. 10, 2010 | Sep. 21, 2010 | III | II | n.d. | n.d. |
| GT | 56 | Sep. 14, 2010 | Dec. 14, 2010 | III D | II | n.d. | n.d. |
| BM | 40 | Aug. 20, 2010 | Nov. 10, 2010 | III D | II | n.d. | n.d. |
| MP | 47 | Jul. 30, 2010 | Nov. 16, 2010 | III D | III | D pos. | pos. |
| GS | 38 | Aug. 19, 2010 | Dec. 14, 2010 | III D | II | n.d. | n.d. | n.d.: not determined
n.a.: not available
neg.: negative
pos.: positive

By the application of the acidified sodium selenite gel in two patients it could be shown that the gel exhibits an effect according to the present invention and may be used in the treatment of cervical dysplasia in an efficient manner.

Example 4: Treatment of a Squamous Cell
Carcinoma of the *Cervix Uteri* in a 38-Year-Old
Patient With Acidified Sodium Selenite Gel
(Prepared According to Example 1)

Due to a pronounced dysplasia of the uterus (stage PAP IV, bioptic according to CIN 3) patient IG, born on 31 Dec. 1975, was subjected to a conization and a curettage of the cervix during her hospitalization period from 29 May 2008 to 2 Jun. 2008 at a general public hospital in Austria. Further examinations, including the histological examination of a tissue sample obtained from the patient, resulted in the diagnosis of an invasive squamous cell carcinoma of the *Cervix uteri* and of a carcinoma in situ with stage FIGU IB 1. This result was confirmed in a subsequent in-patient stay at the gynecological department of another Austrian hospital.

CT, MRI and sonographic examinations resulted in the diagnosis of an obviously malign tumor with a size of 10 to 12 mm located in the cranial region of the *Cervix uteri*, already spreading to the *Isthmus uteri*, but yet without lymphogenic metastatic spread. Not least because of the location of the residual tumor in the region of the *Isthmus uteri*, these results led to a therapeutic recommendation for radical surgery according to Wertheim PIVER II as any uterus-preserving surgery was not possible given the location of the tumor. Despite the enormous time pressure for making a decision, the patient obtained a second medical opinion and finally decided to undergo a potentially uterus-preserving therapy with the preparation according to the present invention. After a four-month period of therapy with the gel according to the present invention, a continuous gynecological, radiological and histological monitoring of the patient yielded a substantial reduction in tumor size as well as a remission of the inflammation. After two further months of therapy with the preparation according to the present invention the tumor had vanished and the histological smear yielded a remission of the inflammation to PAP II+.

What is claimed is:

1. A method comprising:
obtaining a Pap smear from a subject;
determining the result of the Pap smear, wherein the result is an abnormal result, wherein the abnormal result comprises a PAP III result;
obtaining a pharmaceutical composition which is an acidified selenite gel with a pH of less than 5 with selenite at a concentration of 10 mg to 500 mg selenite per 100 g of the composition and at least one pharmaceutically acceptable acid, further defined as citric acid, acetic acid, malic acid, carbonic acid, sulfuric acid, nitric acid, hydrochloric acid, or a fruit acid, dispersed in the acidified selenite gel, wherein the acidified selenite gel comprises an aqueous gelling agent, wherein the total gelling agent concentration in the acidified selenite gel is between 0.1 g to 30 g per 100 g of the composition; and
administering the composition to the subject, wherein said administering is further defined as intravaginal administration;
wherein human papillomavirus (HPV) infection status of the subject is not determined before said administering.

2. The method of claim 1, wherein the aqueous gelling agent is a cellulose derivative.

3. The method of claim 2, wherein the gelling agent is further defined as carboxymethylcellulose, hydroxypropylcellulose, methylcellulose and hydroxyethylcellulose.

4. The method of claim 1, wherein the composition comprises highly dispersed silicon dioxide.

5. The method of claim 1, wherein the composition has a pH between 4.0 and 2.5.

6. The method of claim 1, wherein the composition further comprises at least one buffer substance, coloring agent, stabilizer, and/or carrier substance.

7. The method of claim 1, wherein the composition further comprises at least one antibiotic, antiviral agent, antimycotic, pain inhibitor, and/or anti-inflammatory agent.

8. The method of claim 1, wherein the acid is further defined as citric acid.

9. The method of claim 1, wherein the selenite is a sodium selenite.

10. A method comprising:
obtaining a Pap smear from a subject;
determining the result of the Pap smear, wherein the result is a PAP score of PAP III;
obtaining a pharmaceutical composition which is an acidified selenite gel with selenite at a concentration of 10 mg to 500 mg selenite per 100 g of the composition, silicon dioxide, and at least one pharmaceutically acceptable acid, further defined as citric acid, acetic acid, malic acid, carbonic acid, sulfuric acid, nitric acid, hydrochloric acid, or a fruit acid, dispersed in the acidified selenite gel, wherein the acidified selenite gel comprises an aqueous gelling agent, wherein the total gelling agent concentration in the acidified selenite gel is between 0.1 g to 30 g per 100 g of the composition, and
administering the composition to the subject, wherein said administering is further defined as intravaginal administration;
wherein HPV infection status of the subject is not determined before said administering.

11. The method of claim 1, wherein the composition comprises 0.005 g to 0.1 g of sodium selenite pentahydrate per 100 g of the composition.

12. The method of claim 11, wherein the composition comprises 0.01 g to 0.1 g of sodium selenite pentahydrate per 100 g of the composition.

13. The method of claim 1, further comprising the steps of obtaining a second Pap smear from the subject after the administering, and determining the result of the second Pap smear.

14. The method of claim 12, wherein the pharmaceutical composition is administered at most once per day.

15. The method of claim 10, further comprising the steps of obtaining a second Pap smear from the subject after the administering, and determining the result of the second Pap smear.

16. The method of claim 10, wherein the pharmaceutical composition comprises 0.01 g to 0.1 g of sodium selenite pentahydrate per 100 g of the composition and the pharmaceutical composition is administered at most once per day.

17. The method of claim 13, wherein the result of the second Pap smear is a PAP score less than PAP III.

18. The method of claim 15, wherein the result of the second Pap smear is a PAP score less than PAP III.

* * * * *